United States Patent [19]

Leibinsohn

[11] 4,232,677
[45] Nov. 11, 1980

[54] MICROBE-BARRIER DRAINAGE DEVICE

[76] Inventor: Saul Leibinsohn, 11 Oley Hagardom, Rishon Lezion, Israel

[21] Appl. No.: 908,279

[22] Filed: May 22, 1978

[30] Foreign Application Priority Data

Jun. 7, 1977 [IL] Israel .................................. 52266

[51] Int. Cl.³ .......................... A61F 5/44; A61M 27/00
[52] U.S. Cl. .............................. 128/350 R; 128/274; 128/295
[58] Field of Search ............... 128/349, 350, 275, 294, 128/295, 274

[56] References Cited

U.S. PATENT DOCUMENTS

| | | | |
|---|---|---|---|
| 3,396,727 | 8/1968 | Mount | 128/349 R |
| 3,417,750 | 12/1968 | Carson | 128/349 R |
| 3,797,478 | 3/1974 | Walsh et al. | 128/349 R X |
| 3,848,603 | 11/1974 | Throner | 128/349 R |
| 3,976,311 | 8/1976 | Spendlove | 128/349 R X |

FOREIGN PATENT DOCUMENTS 119625 2/1971 Denmark .................................. 128/275

Primary Examiner—Dalton L. Truluck
Attorney, Agent, or Firm—Benjamin J. Barish

[57] ABSTRACT

A microbe barrier device particularly useful for draining body liquids while avoiding retrograde infection is described, comprising a housing including an inlet connectable to a liquid line and an outlet through which the liquid from the line is drained, a one-way valve within the housing between its inlet and outlet and permitting the one-way flow of the liquid only from the inlet to the outlet, and a barrier within the housing between its inlet and the one-way valve and including an antiseptic substance in contact with all surfaces of the inlet side of the valve through which the liquid flows.

5 Claims, 3 Drawing Figures

U.S. Patent   Nov 11, 1980   4,232,677
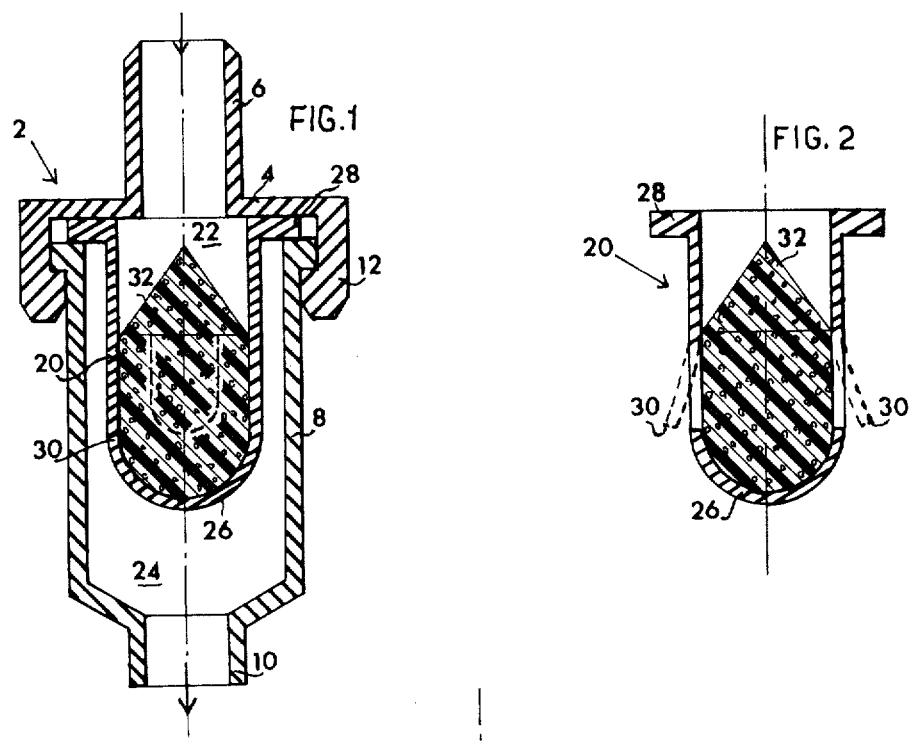
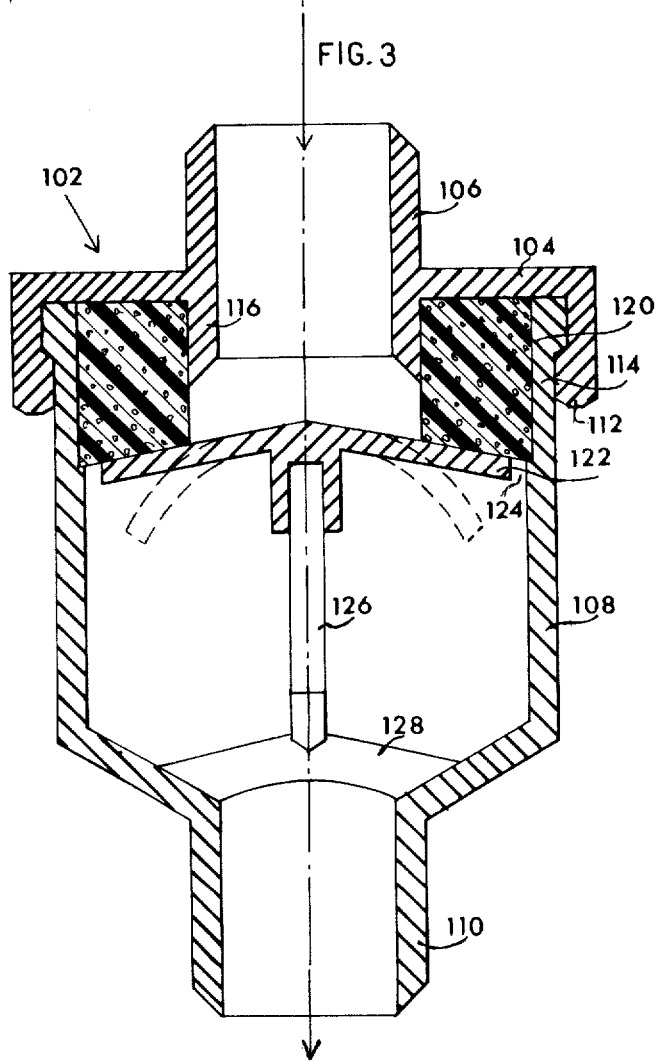

MICROBE-BARRIER DRAINAGE DEVICE

BACKGROUND OF THE INVENTION

The present invention relates to a microbe-barrier device, and particularly to such a device useful for draining body fluids while avoiding retrograde infection.

Drip-chambers are commonly used in drainage lines to prevent retrograde infection when draining body fluids (e.g. urine) from a human patient. The drip chambers, usually connected to the drainage tube between the patient and the container (e.g. plastic sack) receiving the drainage fluids, produce a break in the flow path of the liquid and thereby prevent retrograde or backward movement of microbes towards the human patient.

An object of the present invention is to provide a new form of microbe-barrier particularly useful for draining body liquids and more effectively avoiding retrograde infection.

SUMMARY OF THE INVENTION

According to the present invention, there is provided a microbe-barrier device particularly useful for the above purpose, comprising: a housing including an inlet connectable to a liquid line and an outlet through which the liquid from the line is drained; a one-way valve within the housing between its inlet and outlet and permitting the one-way flow of the liquid only from the inlet to the outlet; and a barrier within the housing between its inlet and the one-way valve and including an antiseptic substance in contact with all surfaces of the inlet side of the valve through which the liquid flows.

In the preferred embodiments of the invention described below, the barrier comprises a sponge impregnated with said antiseptic substance.

Two embodiments of the invention are described below. In one described embodiment, the one-way valve comprises an elastomeric membrane secured within the housing and partitioning its interior into an upper inlet chamber communicating with the housing inlet, and a lower outlet chamber communicating with the housing outlet. The membrane is formed with a central pocket at its lower end which pocket is slitted to permit liquid flow only from the inlet chamber to the outlet chamber. The barrier is disposed within this pocket in contact with all the slit edges of the membrane.

In a second described embodiment, the barrier is of annular shape and is disposed around the complete circumference of the inner face of the housing adjacent its inlet. The oneway valve comprises a resilient conical member of smaller diameter than the inner face of the housing wall so as to be slightly spaced therefrom. The conical member is supported by a stem such that the upper face of the conical member is normally in light contact with the lower edge of the barrier but is displaceable therefrom by a liquid entering the housing inlet to permit the flow of the liquid between the annular barrier and the conical member to the housing outlet.

Further features and advantages of the invention will be apparent from the description below.

BRIEF DESCRIPTION OF THE DRAWINGS

The invention is herein described, by way of example only, with reference to the accompanying drawings, wherein:

FIG. 1 is a vertical sectional view of one form of microbebarrier device constructed in accordance with the present invention;

FIG. 2 is a similar view illustrating only the oneway valve in the device of FIG. 1; and FIG. 3 is a vertical sectional view of a second form of microbe-barrier contructed in accordance with the invention.

DESCRIPTION OF THE PREFERRED EMBODIMENTS

The microbe-barrier illustrated in FIG. 1 comprises a housing, generally designated 2, constituted of an upper section 4 including an inlet 6 connectable to a liquid line (not shown), and a lower section 8 including an outlet 10 through which the liquid from the line is drained. Housing section 4 is of disc-shape and is formed with an annular outturned rim 12 at its outer periphery. Housing section 8 is of substantially cylindrical shape and is formed at its upper end with an annular flange 14 adapted to be attached, as by a snap-fit, into the outturned rim 12 of housing section 4.

An elastomeric (e.g. natural or synthethic rubber) membrane 20 is secured within housing 2 and partitions its interior into an inlet chamber 22 communicating with the housing inlet 6, and an outlet chamber 24 communicating with the housing outlet 10. Membrane 20 may be in the form of a rubber finger or tube closed at one end 26 defining a depending pocket, and open at the opposite end 28 for securement between the two housing sections 4 and 8. The opposite walls in the lower pocket portion 26 of membrane 20 are formed with slits 30, preferably semi-circular in configuration, the upper open edges of the slits being about mid-way of the height of membrane 20, and the lower curved end of the slits being about one-third the height of the membrane. Slits 30 permit the liquid to flow through the membrane 20 only in one direction, that is from the inlet chamber 22 to the outlet chamber 24, and not visa versa.

Also disposed within housing 2 is an antiseptic member 32, in the form of a sponge impregnated with an antiseptic substance, such as thymol or other germicide. The impregnated sponge 32 is received within the pocket portion 26 of the elastomeric membrane 20 so as to engage and cover all the edges of its slits 30.

The device illustrated in FIGS. 1 and 2 is used as follows: Housing inlet 6 is press-fitted into the end of the rubber tube connected to the patient for receiving the liquids being drained from the patient, which liquid drains through the housing outlet 10. As liquid is received within the housing inlet chamber 22, it is permitted to pass through slits 30 in the rubber diaphragm 20 into the housing outlet chamber 24, from which it drains through the housing outlet 10. FIG. 2 illustrates how the slits 30 are opened to permit the liquid to pass, and it will be seen that the slits permit the liquid to pass through the membrane 20 only in the direction from inlet chamber 22 to the outlet chamber 24, and not visa versa. Since all the edges of slits 30 through which the liquid may flow from chamber 22 to chamber 24 are in contact with the antiseptic substance in the impregnated sponge 32, any microbes that may be in the outlet chamber 24 are prevented from passing into the inlet chamber 22, thereby keeping inlet chamber 22 sterile. Accordingly, sponge 32, impregnated with the antiseptic substance, acts as a barrier preventing retrograde infection of the patient.

The device illustrated in FIG. 3 accomplishes the same result as described above but includes a different construction.

In FIG. 3, the housing, generally designated 102, also includes two sections, namely an upper section 104 formed with an inlet 106, and a lower section 108 including the outlet 110, the two sections being snap-fitted together by an annular shoulder 112 formed at the lower end of the upper housing section 104 received with a recess 114 in the lower housing section 108. In this case, however, the upper housing section 104 is formed with an annular wall 116 extending axially of the housing coaxial with inlet 106. Wall 116 is spaced radially inwardly of, but extends coaxial with, the outer annular wall of the lower housing section 108, and thus forms an annular space between it and the outer housing wall.

The microbe barrier sponge 120 is also of annular shape and is disposed within the annular space between wall 116 and housing 108. As in FIGS. 1 and 2, sponge 120 is impregnated with an antiseptic substance.

The one-way valve disposed within housing 106 is in the form of a resilient conical member 122 of slightly smaller diameter than the lower housing section wall 108 so as to be spaced from it as shown at 124. It is supported by a stem 126 which in turn is secured to a diametral rib 128 extending across outlet opening 110.

The resilient conical valve member 122 is so dimensioned that its upper face is normally in contact with the lower edge of the microbe-barrier sponge 120, but is spaced from the lower edge of the annular housing wall 116 and is also spaced from the lower housing annular wall 108, as shown at 124. Accordingly, liquid entering the housing via inlet 106 would tend to accummulate on the upper face of conical valve member 122, and eventually would cause the outer periphery of the valve member to flex (as shown in broken lines), permitting the liquid to flow from the inlet side of the housing to the outlet side. It will be appreciated that the conical member 122 permits the flow only in this direction, and prevents the flow in the reverse direction, namely from the outlet side to the inlet side. Moreover, it will be seen that the antiseptic substance in the microbe-barrier sponge 120 is in contact with the upper face of the conical valve member 122, thereby keeping the inlet side of the housing always sterile and preventing retrograde infection.

An advantage in the arrangement of FIG. 3 is that the annular wall 116 is effective to shield most of the surface of the microbe-barrier sponge 120 from contact with the liquid being drained from the patient, thereby minimizing the washing-out of the antiseptic substance with which it is impregnated, and increasing the useful life of the device before requiring replacement or reimpregnation of the microbe-barrier sponge.

While the invention has been described with respect to two preferred embodiments, it will be appreciated that these are described for purposes of example and that many variations, modifications and other applicatons of the invention may be made.

What is claimed is:

1. A microbe barrier device particularly useful for draining body liquids while avoiding retrograde infection, comprising: a housing including an inlet connectable to a liquid line and an outlet through which the liquid from the line is drained; a one-way valve within the housing between its inlet and outlet and permitting the one-way flow of the liquid only from the inlet to the outlet; and a barrier within the housing between its inlet and the one-way valve and including an antiseptic substance in contact with all surfaces of the inlet side of the valve through which the liquid flows, said one-way valve comprising an elastomeric membrane secured within the housing and partitioning its interior into an upper inlet chamber communicating with the housing inlet, and a lower outlet chamber communicating with the housing outlet; said membrane being formed with a central pocket at its lower end which pocket is slitted to permit liquid flow only from the inlet chamber to the outlet chamber; said barrier being disposed within said pocket in contact with all the slit edges of the membrane.

2. A device according to claim 1, wherein said barrier comprises a sponge impregnated with said antiseptic substance.

3. A device according to claim 1, wherein said housing includes two sections secured together, one section being formed with the housing inlet and the other section being formed with the housing outlet, the outer periphery of said membrane being secured between said two housing sections.

4. A microbe barrier device particularly useful for draining body liquids while avoiding retrograde infection, comprising: a housing including an inlet connectable to a liquid line and an outlet through which the liquid from the line is drained; a one-way valve within the housing between its inlet and outlet and permitting the one-way flow of the liquid only from the inlet to the outlet; and a barrier within the housing between its inlet and the one-way valve and including an antiseptic substance in contact with all surfaces of the inlet side of the valve through which the liquid flows, whrein said barrier is of annular shape and is disposed around the complete cicumference of the inner face of the housing adjacent its inlet; said one-way valve comprisig a resilient conical member of smaller diameter than the inner face of the housing wall so as to be slightly spaced therefrom, said conical member being supported by a stem such that the upper face of the conical member is normally in light contact with the lower edge of the barrier but is displaceable therefrom by a liquid entering the housing inlet to permit the flow of said liquid between the annular barrier and the conical member to the housing outlet.

5. A device according to claim 4, wherein said housing includes an annular wall coaxial with, and spaced axially inwardly of, the housing inlet, but terinating short of the conical member; said annular barrier being disposed in the space between the housing and said annular wall with its upper portion shielded by said wall, and its lower edge in contact with the conical member.

* * * * *